US012104202B2

(12) United States Patent
Osborne et al.

(10) Patent No.: US 12,104,202 B2
(45) Date of Patent: *Oct. 1, 2024

(54) METHOD OF IDENTIFYING SEQUENCE VARIANTS USING CONCATENATION

(71) Applicant: OXFORD NANOPORE TECHNOLOGIES PLC, Oxford (GB)

(72) Inventors: Robert Osborne, Saffron Walden (GB); Esther Musgrave-Brown, Cambridge (GB)

(73) Assignee: OXFORD NANOPORE TECHNOLOGIES PLC, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/394,797

(22) Filed: Aug. 5, 2021

(65) Prior Publication Data

US 2022/0033885 A1 Feb. 3, 2022

Related U.S. Application Data

(63) Continuation of application No. 16/693,042, filed on Nov. 22, 2019, now Pat. No. 11,111,524, which is a
(Continued)

(30) Foreign Application Priority Data

Sep. 2, 2015 (GB) .................................. 1515558

(51) Int. Cl.
*C12Q 1/6827* (2018.01)
*C12Q 1/6869* (2018.01)
*G16B 30/00* (2019.01)

(52) U.S. Cl.
CPC ......... *C12Q 1/6827* (2013.01); *C12Q 1/6869* (2013.01); *G16B 30/00* (2019.02)

(58) Field of Classification Search
CPC ............ C12Q 1/6869; C12Q 2521/501; C12Q 2535/122; C12Q 1/6827
See application file for complete search history.

(56) References Cited

U.S. PATENT DOCUMENTS 10,519,488 B2 * 12/2019 Osborne .............. C12Q 1/6869
11,111,524 B2 * 9/2021 Osborne .............. C12Q 1/6827
(Continued)

FOREIGN PATENT DOCUMENTS

CA         2933343        6/2015
WO    WO 2005/079357     9/2005
(Continued)

OTHER PUBLICATIONS

Patino et al., "Serial Analysis of Gene Expression: Technical Considerations and Applications to Cardiovascular Biology," Circulation Research, vol. 91, pp. 565-569. (Year: 2002).*

(Continued)

*Primary Examiner* — Young J Kim
(74) *Attorney, Agent, or Firm* — James S. Keddie; Bozicevic, Field & Francis LLP

(57) ABSTRACT

Described herein, among other things, is a method of sequencing, comprising: concatenating a plurality of fragments of genomic DNA to produce concatenated DNA; sequencing the concatenated DNA to produce a plurality of sequence reads, wherein at least some of the sequence reads comprise: at least the sequence of the 3' and/or 5' ends of a fragment that corresponds to the locus of interest and sequence of one or both of the fragments that flank the fragment in the concatenated DNA; and grouping the sequence reads that corresponds to the locus of interest using, for each of the grouped sequence reads: the 3' and/or 5' end sequences; and/or the flanking sequence.

12 Claims, 2 Drawing Sheets

Related U.S. Application Data continuation of application No. 15/756,051, filed as application No. PCT/IB2016/055252 on Sep. 1, 2016, now Pat. No. 10,519,488.

(56) References Cited

U.S. PATENT DOCUMENTS

| | | | |
|---|---|---|---|
| 2006/0134650 A1* | 6/2006 | Gunderson | C12Q 1/6827 435/6.12 |
| 2006/0177832 A1 | 8/2006 | Brenner | |
| 2006/0177833 A1 | 8/2006 | Brenner | |
| 2013/0073214 A1 | 3/2013 | Hyland et al. | |
| 2016/0306923 A1 | 10/2016 | van Rooyen et al. | |

FOREIGN PATENT DOCUMENTS

| | | | |
|---|---|---|---|
| WO | WO-2013096802 A1 * | 6/2013 | C12N 15/1096 |
| WO | WO 2015/083004 | 6/2015 | |

OTHER PUBLICATIONS

Parkinson et al., "Preparation of high-quality next-generation sequencing libraries from picogram quantities of target DNA," Genome Research, vol. 22, pp. 125-133. (Year: 2012).*

Brinkman et al., "Whole-genome DNA methylation profiling using MethylCap-seq," Methods, vol. 52, pp. 232-236. (Year: 2010).*

Hiatt et al., "Parallel, tag-directed assembly of locally derived short sequence reads," Nature Methods, February, vol. 7, No. 2, pp. 119-122 and On-line methods pp. 1-3 (Year: 2010).*

Hayden et al., "Sequence-tagged microsatellite profiling (STMP): a rapid technique for developing SSR markers", Nucleic Acids Research, 2001, 29(8):e43.

Hsu et al., "AmpliVar: Mutation Detection in High-Throughput Sequence from Amplicon-Based Libraries", Human Mutation, 2015, 36(4):411-418.

Kinde et al., "Detection and quantification of rare mutations with massively parallel sequencing", Proceedings of the National Academy of Sciences, 2011, 108(23): 9530-9535.

Meacham et al., "Identification and correction of systematic error in high-throughput sequence data", BMC Bioinformatics, 2011, 12:451.

Newman et al., "An ultrasensitive method for quantitating circulating tumor DNA with broad patient coverage", Nature Medicine., 2014, 20(5): 548-554.

Schmitt et al., "Detection of ultra-rare mutations by next-generation sequencing", Proceedings of the National Academy of Sciences, 2012, 109(36): 14508-14513.

Shugay et al., "Towards error-free profiling of immune repertoires", Nature Methods, Advance Online Publication, 2014, 653-655.

* cited by examiner

METHOD OF IDENTIFYING SEQUENCE VARIANTS USING CONCATENATION

CROSS-REFERENCING

This application is a continuation of U.S. application Ser. No. 16/693,042, filed on Nov. 22, 2019, which is a continuation of U.S. application Ser. No. 15/756,051, filed on Feb. 27, 2018, which is a § 371 national phase of International Application No. PCT/IB2016/055252, filed on Sep. 1, 2016, which claims the benefit of UK patent application serial no. 1515558.3, filed on Sep. 2, 2015, which applications are incorporated by reference herein.

BACKGROUND

Many diseases are caused by somatic mutations. Because somatic mutations only occur in a fraction of the cells in the body, they can be difficult to detect with high sensitivity and specificity by next generation sequencing. One problem is that every library preparation method and sequencing platform results in sequence reads that contain errors, e.g., PCR errors and sequencing errors. While it is sometimes possible to correct systematic errors (e.g., those that are correlated with known parameters including sequencing cycle-number, strand, sequence-context and base substitution probabilities), it is often impossible to figure out with any certainty whether a variation in a sequence is caused by an error or if it is a "real" mutation. This problem is exacerbated in samples in which the sample has low diversity and/or mutation-containing polynucleotides are present only at relatively low levels, e.g., less than 5%, in the sample. For example, if a sample contains only one copy of a mutation-containing polynucleotide in a background of hundreds of polynucleotides that are otherwise identical to the mutation-containing polynucleotide except that they do not contain the mutation, then, after those polynucleotides have been sequenced, it is often impossible to tell whether the variation (which may only be observed in about $^1/_{100}$ of the sequence reads) is an error that occurred during amplification or sequencing. Thus, the detection of somatic mutations that cause diseases can be extremely difficult to detect with any certainty.

SUMMARY

Described herein, among other things, is a method of sequencing, comprising: concatenating a plurality of fragments of genomic DNA to produce concatenated DNA; sequencing fragments of the concatenated DNA, or amplification products thereof, to produce a plurality of sequence reads, wherein at least some of the sequence reads comprise: at least the sequence of the 3' and/or 5' ends of a fragment that corresponds to the locus of interest; and sequence of one or both of the fragments that flank the fragment in the concatenated DNA; and grouping the sequence reads that corresponds to the locus of interest using, for each of the grouped sequence reads: the 3' and/or 5' end sequences; and/or the flanking sequence.

As will be described in greater detail below (and illustrated in FIG. 1), the method can be used to ascertain if a sequence variation is genuine. In these embodiments, the method may further comprise: determining which groups of sequence reads contain a potential sequence variation for the locus of interest; and calculating a probability that the potential sequence variation is a genuine mutation or an artifact using: (i) the number of reads in the group that contain the potential sequence variation, (ii) the number of groups that contain the potential sequence variation, and (iii) the total number of groups corresponding to the locus of interest.

The method finds particular use in analyzing samples in which DNA has limited diversity and that also contain fragments having a low copy number mutation (e.g., a sequence caused by a mutation that is present at low copy number relative to sequences that do not contain the mutation), which are both features of many patient samples that can be obtained non-invasively, such as circulating, cell-free DNA (e.g., ctDNA) samples, which can be obtained from peripheral blood, or invasively, e.g., tissue sections. In such samples, the mutant sequences may only be present at a very limited copy number (e.g., less than 10, less than 5 copies or even 1 copy in a background of hundreds or thousands of copies of the wild type sequence) and there is a high probability that at least some of the mutant fragments have an otherwise identical sequence (including identical end sequence(s)) to a wild type fragment. In these situations, it can be very difficult to identify a sequence variation with significant confidence.

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
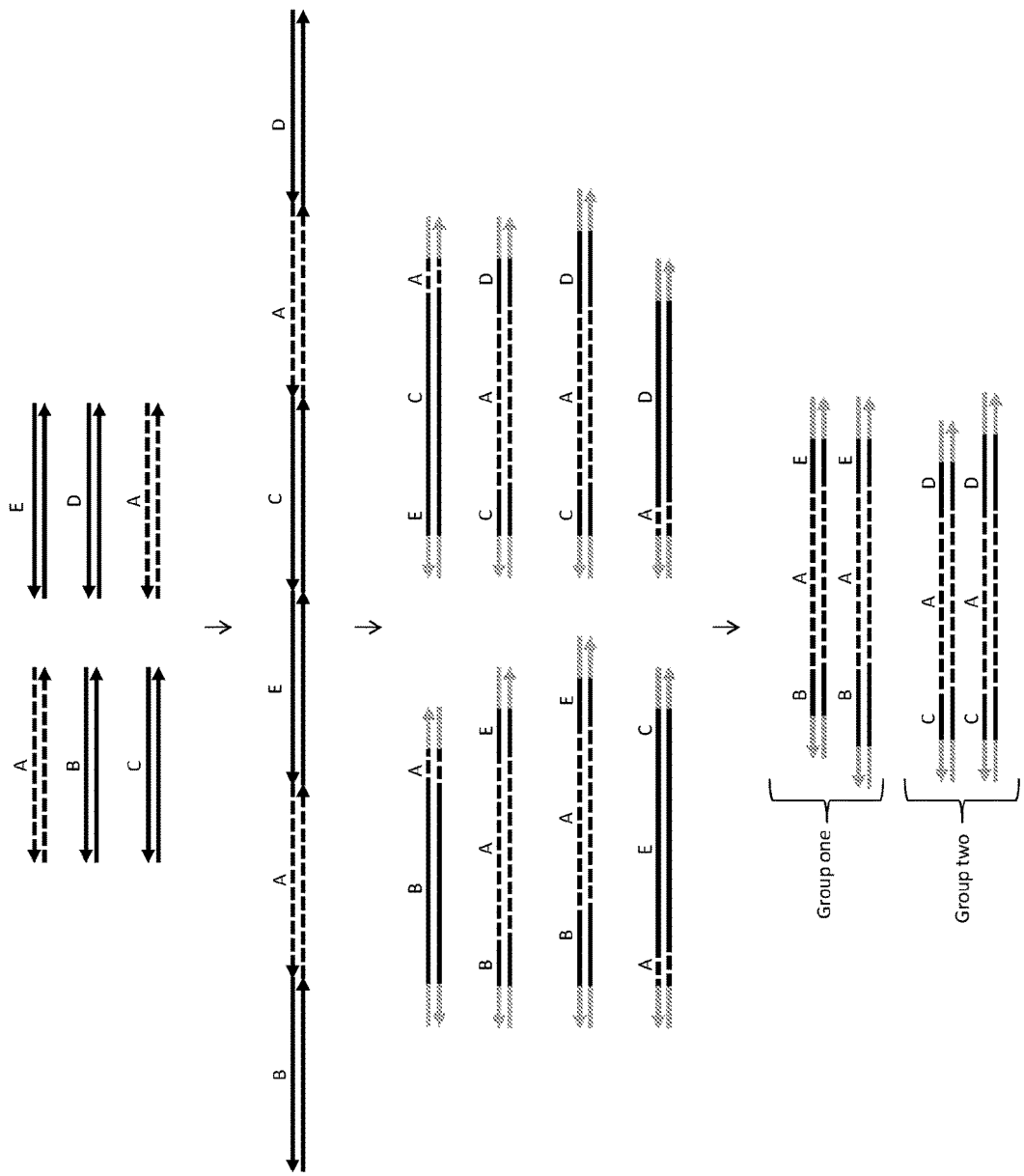
FIG. 1 schematically illustrates some of the principles of the present method. Note that there are two A molecules (with identical 5'/3' breakpoints) shown by dashed lines. The fragments are concatenated. The two A molecules have different flanking fragments. The concatemers are then amplified or, optionally, fragmented and amplified. The light grey sequences are adaptors. After sequencing reads can be grouped according to 5'/3' breakpoints and the flanking sequences. This allows both A sequences to be individually identified.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment.

The term "nucleic acid sample," as used herein, denotes a sample containing nucleic acids. Nucleic acid samples used herein may be complex in that they contain multiple different molecules that contain sequences. Genomic DNA samples from a mammal (e.g., mouse or human) are types of complex samples. Complex samples may have more than about $10^4$, $10^5$, $10^6$ or $10^7$, $10^8$, $10^9$ or $10^{10}$ different nucleic acid molecules. A DNA target may originate from any source such as genomic DNA, or an artificial DNA construct. Any sample containing nucleic acid, e.g., genomic DNA from tissue culture cells or a sample of tissue, may be employed herein.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, greater than 10,000 bases, greater than 100,000 bases, greater than about 1,000,000, up to about $10^{10}$ or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid," or "UNA," is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 81 to 100, 101 to 150 or 151 to 200 nucleotides in length, for example.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded or partially double-stranded. If double-stranded, the primer is usually first treated to separate its strands before being used to prepare extension products. This denaturation step is typically effected by heat, but may alternatively be carried out using alkali, followed by neutralization. Also included in this definition are toehold exchange primers, as described in Zhang et al (Nature Chemistry 2012 4: 208-214), which is incorporated by reference herein.

Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a region of nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strand regions in a hybridization reaction. The hybridization reaction can be made to be highly specific by adjustment of the hybridization conditions (often referred to as hybridization stringency) under which the hybridization reaction takes place, such that two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotide region that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acids, which are produced from the amplifying process as defined herein. DNA can be amplified by isothermal amplification methods or by PCR for example. In some embodiments, DNA can be amplified by a whole genome amplification (WGA method).

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "copies of fragments" refers to the product of amplification, where a copy of a fragment can be a reverse complement of a strand of a fragment, or have the same sequence as a strand of a fragment.

The term "substantially identical sequences" refers to sequences that are at least 95% or at least 99% identical to one another.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary," they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The term "extending", as used herein, refers to the extension of a primer by the addition of nucleotides using a polymerase. If a primer that is annealed to a nucleic acid is extended, the nucleic acid acts as a template for extension reaction.

The terms "A-tailed", "C-tailed", "G-tailed", and "T-tailed", as used herein, refer to fragments with single-base 3' overhangs. If added enzymatically, typically these overhangs are generated via the non-template addition by a polymerase of a single nucleotide to the 3' end of a blunt fragment, but other methods may also be used. Alternatively 3' overhangs may be generated when annealing two oligonucleotides.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing", as used herein, refer to the so-called parallelized sequencing-by-synthesis or sequencing-by-ligation platforms currently employed by Illumina, Life Technologies, and Roche, etc. Next-generation sequencing methods may also include nanopore sequencing methods such as those commercialized by Oxford Nanopore Technologies, electronic-detection based methods such as Ion Torrent technology commercialized by Life Technologies, or single-molecule fluorescence-based methods commercialized by Pacific Biosciences.

The term "asymmetric adaptor", as used herein, refers to an adaptor that, when ligated to both ends of a double stranded nucleic acid fragment, will lead to a top strand that contains a 5' tag sequence that is not the same as or complementary to the tag sequence at the 3' end. Exemplary asymmetric adapters are described in: U.S. Pat. Nos. 5,712,126 and 6,372,434 and WO/2009/032167; all of which are incorporated by reference herein in their entirety. An asymmetrically tagged fragment can be amplified by two primers: one that hybridizes to a first tag sequence added to the 3' end of a strand, and another that hybridizes to the complement of a second tag sequence added to the 5' end of a strand. Y-adaptors and hairpin adaptors (which can be cleaved, after ligation, to produce a "Y-adaptor") are examples of asymmetric adaptors.

The term "Y-adaptor" refers to an adaptor that contains: a double-stranded region and a single-stranded region in which the opposing sequences are not complementary. The end of the double-stranded region can be joined to target molecules such as double-stranded fragments of genomic DNA, e.g., by ligation or a transposase-catalyzed reaction. Each strand of an adaptor-tagged double-stranded DNA that has been ligated to a Y adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence.

The term "hairpin adaptor" refers to an adaptor that is in the form of a hairpin. In one embodiment, after ligation the hairpin loop can be cleaved to produce strands that have non-complementary tags on the ends. In some cases, the loop of a hairpin adaptor may contain a uracil residue, and the loop can be cleaved using uracil DNA glycosylase and endonuclease VIII, although other methods are known.

The term "tagging" as used herein, refers to the appending of a sequence tag (that contains an identifier sequence) onto a nucleic acid molecule. A sequence tag may be added to the 5' end, the 3' end, or both ends of nucleic acid molecule. A sequence tag can be added to a fragment by ligating an oligonucleotide to the fragment.

The terms "identifier sequence" and "tag sequence that identifies" are used interchangeably herein to, refer to a sequence of nucleotides used to identify and/or track the source of a polynucleotide in a reaction. After the polynucleotides in a sample are sequenced, the identifier sequence can be used to distinguish the sequence reads and/or determine from which sample a sequence read is derived. An "identifier sequence" may be referred to a "sample barcode", "index" or "indexer" sequence in other publications. For example, different samples (e.g., polynucleotides derived from different individuals, different tissues or cells, or polynucleotides isolated at different times points), can be tagged with identifier sequences that are different from one another and, after the samples are tagged, they are pooled. After sequencing, the source of a sequence can be tracked back to a particular sample using the identifier sequence. Identifier sequences can be added to a sample by ligation, by primer extension using a tailed primer that contains an identifier sequence in a 5' tail, or using a transposon. An identifier sequence can range in length from 2 to 100 nucleotide bases or more and may include multiple subunits, where each different identifier has a distinct identity and/or order of subunits. A sample identifier sequence may be added to the 5' end of a polynucleotide or the 3' end of a polynucleotide, for example. In particular embodiments, a barcode sequence may have a length in range of from 1 to 36 nucleotides, e.g., from 6 to 30 nucleotides, or 8 to 20 nucleotides. In certain cases, the molecular identifier sequence may be error-correcting, meaning that even if there is an error (e.g., if the sequence of the molecular barcode is mis-synthesized, mis-read or is distorted by virtue of the various processing steps leading up to the determination of the molecular barcode sequence) then the code can still be interpreted correctly. Descriptions of exemplary error correcting sequences can be found throughout the literature (e.g., US20100323348 and US20090105959, which are both incorporated herein by reference). In some embodiments, an identifier sequence may be of relatively low complexity (e.g., may be composed of a mixture of 8 to 1024 different sequences), although higher complexity identifier sequences can be used in some cases.

The term "sample identifier sequence" is a sequence of nucleotides that is appended to a target polynucleotide, where the sequence identifies the sample (e.g., which individual, which cell, which tissue, or which times points, etc.) from which a sequence read is derived. In use, each sample is tagged with a different sample identifier sequence (e.g., one sequence is appended to each sample, where the different samples are appended to different sequences), and the tagged samples can be pooled. After the samples are sequenced, the sample identifier sequence can be used to identify the source of the sequences.

As used herein, the term "complementary" in the context of sequence reads that are complementary, refers to reads for sequences that, after the sequences have been trimmed to remove adaptor sequences, are substantially complementary to one another and, in some cases, have identical or near identical ends, indicating that the reads are derived from the same initial template molecules.

The term "identical or near-identical sequences", as used herein, refers to near duplicate sequences, as measured by a similarity function, including but not limited to a Hamming distance, Levenshtein distance, Jaccard distance, cosine distance etc. (see, generally, Kemena et al, Bioinformatics 2009 25: 2455-65). The exact threshold depends on the error rate of the sample preparation and sequencing used to perform the analysis, with higher error rates requiring lower thresholds of similarity. In certain cases, substantially identical sequences have at least 98% or at least 99% sequence identity.

The term "fragmentation breakpoint" is intended to refer to the site at which a nucleic acid is cleaved to produce a fragment. Two fragments that have the same fragmentation breakpoints have the same sequences at their ends (excluding any exogenous sequences that have been added to the fragments). Fragmentation breakpoints can be generated by random or non-random methods. In analyzing sequence reads, the fragmentation breakpoint may be identified as the boundary between genomic-derived sequence and adaptor derived sequences (including or excluding any overhangs in adaptor sequences).

The term "identical or near-identical fragmentation breakpoints", as used herein, refers to two molecules that have the same 5' end, the same 3' end, or the same 5' and 3' ends, where the differences in sequence are due to a PCR error, a sequencing error or a mutation. A fragmentation breakpoint can be determined by removing non-target sequences from a sequence read, leaving the sequence of the target. The first nucleotide of the trimmed sequence represents the first nucleotide after the fragmentation breakpoint. In sequencing an amplified sample, two sequence reads that correspond to fragments that have identical or near-identical fragmentation breakpoints can be derived from the same initial fragment. In many cases, 8-30 nucleotides at the end of a trimmed sequence can be compared to the ends of other trimmed sequences to determine if the fragmentation breakpoints are the same or different. In many cases, fragmentation breakpoints can be identified after mapping reads to a reference sequence. Fragmentation breakpoints may be mapped using, e.g., Picard MarkDuplicates (available from the Broad Institute)), Samtools rmdup (see, e.g., Li et al. Bioinformatics 2009, 25: 2078-2079) and BioBamBam (Tischler et al, Source Code for Biology and Medicine 2014, 9:13).

The term "pooling", as used herein, refers to the combining, e.g., mixing, of two samples such that the molecules within those samples become interspersed with one another in solution.

The term "pooled sample", as used herein, refers to the product of pooling.

The term "target enrichment", as used herein, refers to a method in which selected sequences are separated from other sequences in a sample. This may be done by hybridization to a probe, e.g., hybridizing a biotinylated oligonucleotide to the sample to produce duplexes between the oligonucleotide and the target sequence, immobilizing the duplexes via the biotin group, washing the immobilized duplexes, and then releasing the target sequences from the oligonucleotides. Alternatively, a selected sequence may be enriched by amplifying that sequence, e.g., by PCR using one or more primers that hybridize to a site that is proximal to the target sequence.

The terms "minority variant" and "sequence variation", as used herein, is a variant that is present a frequency of less than 50%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:100 or less, 1:1,000 or less, 1:10,000 or less, 1:100,000 or less or 1:1,000,000 or less.

The term "concatenating", as used herein, refers to the joining of fragments to one another in a random order and orientation to produce a concatenation product, i.e., single molecule in which the initial fragments, or copies thereof, are covalently linked to one another, either directly or indirectly.

The term "concatenated DNA", as used herein, refers to a product of concatenating fragments of DNA to one another. Such a molecule may contain at least 3, at least 5, at least 10, at least 50, at least 100, at least 500, or at least 1000 fragments that are joined to one another, either directly or indirectly (e.g., via a junction adaptor). A concatenated molecule may be linear or circular. DNA fragments may be concatenated by ligation or overlap extension, for example.

The term "ligating", as used herein, refers to the enzymatically catalyzed joining of the terminal nucleotide at the 5' end of a first DNA molecule to the terminal nucleotide at the 3' end of a second DNA molecule such that the first DNA molecule and the second DNA molecule become covalently linked to one another, either directly or indirectly (e.g., via an intervening sequence such as a junction adaptor).

The term "ligated to one another via junction adaptor", as used herein, refers to the indirect ligation of two or more DNA molecules to one another via an adaptor. A concatenated DNA molecule that contains fragments that have been ligated to one another via a junction adaptor may contain a first fragment, an adaptor, a second fragment, an adaptor, a third fragment, an adaptor, and so on.

The term "overlap extension", as used herein, refers to a way for concatenating DNA fragments together by primer extension. In some embodiments, overlap extension may comprise ligating adaptors onto the ends of the fragments, and then making a concatemer of the adaptor ligated fragments using primers that have 5' tails that hybridize to one another (see, e.g., Horton BioTechniques, Vol. 54, No. 3, March 2013, pp. 129-133) or by designing the adaptors so that they hybridize to one another, and then extending the adaptors using another fragment as a template.

The term "potential sequence variation", as used herein, refers to a sequence variation, e.g., a substitution, deletion, insertion or rearrangement of one or more nucleotides in one sequence relative to another that could potentially be present in the original, unamplified sample. A sequence variation may be a genuine sequence variation or an artifact.

The term "genuine sequence variation", as used herein, refers to a sequence variation that is present in the original, unamplified sample. A genuine sequence variation may be a SNP, or it may be a somatic or germline mutation.

The term "artifact", as used herein, refers to a sequence variation that resulted from an amplification error (i.e., a mis-incorporation of base by the polymerase during amplification) or a miss-call of a base during sequencing. Neither of these mutations are present in the original, unamplified sample and, as such, they are referred to as "artifacts".

As used herein, the term "correspond to", with reference to a sequence read that corresponds to a locus of interest, refers to a sequence read obtained from an amplification product of that locus.

The term "at least the sequence of the 3' and/or 5' ends of a fragment", as used herein, refers to the 3' and/or 5' sequences that are at the ends of the fragment, i.e., immediately adjacent to the fragmentation breakpoint of the fragment. A sequence read that contains at least the sequence of the 3' and/or 5' ends of a fragment may contain at least 10, at least 20, at least 30, at least 50, at least 100 bases at the 3' end of a fragment, and/or at least 10, at least 20, at least 30, at least 50 or at least 100 bases at the 5' end of a fragment. In some embodiments, one sequence read may contain the entire contiguous sequence of one or more fragments, in which case the read may contain sequence from both ends of the fragment. In some cases, the sequence may be a paired end sequence, in which case sequence read may contain only the ends of a fragment or, if the paired end reads are overlapping, the sequence of the entire fragment, including the ends.

The term "flanks", as used herein in the context of a fragment that flanks a fragment of interest, refers to a fragment that is immediately adjacent to the fragment of interest (excluding any adaptor or exogenous sequence that is present between the first and second fragments).

The term "flanking sequence", as used herein, refers to sequence that is obtained from a fragment that flanks a fragment of interest. In some cases, the flanking sequence may be obtained from the end of the second fragment that is joined to the fragment of interest (e.g., at least 10, at least 20, at least 30, at least 50, at least 100 bases at the 3' end or 5' end of the flanking fragment).

The term "whole genome amplification", as used herein, refers to any type of amplification reaction that results in a relatively uniform amplification of substantially all template sequences in a sample (e.g., at least 90% or 95% of the template sequences). Exemplary whole genome amplification methods include degenerate oligonucleotide PCR (DOP-PCR), primer extension preamplification (PEP), and adapter-linker PCR. Whole genome amplification methods of particular interest include multiple displacement amplification ("MDA"; see Dean et al Proc. Natl. Acad. Sci. 2002 99: 5261-5266 and Nelson Biotechniques 2002 Suppl:44-47), as well as multiple annealing and looping based amplification cycles ("MalBac"; see Zong et al Science. 2012 338:1622-1626) and PicoPLEX, which both involve a limited MDA-based pre-amplification followed by PCR (see, e.g., de Bourcy et al, PLoS One. 2014 9: e105585; Arneson et al Oncol. 2012:710692 and Mohlendick et al, Curr Protoc Cell Biol. 2014 65: 1-22).

The term "sequence diversity", as used herein, refers to the number of 5' and/or 3' breakpoints that are associated with a plurality of fragments corresponding to a target sequence.

Other definitions of terms may appear throughout the specification.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), Lehninger, A., *Principles of Biochemistry* 3$^{rd}$ Ed., W. H. Freeman Pub., New York, N.Y. and Berg et al. (2002) *Biochemistry*, 5$^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Some of the principles of the method are shown in FIG. 1. With reference to FIG. 1, the method can be initiated by concatenating a plurality of fragments of genomic DNA to produce concatenated DNA. In this method, the fragments may have a median size that is below 1 kb (e.g., in the range of 50 bp to 500 bp, or 80 bp to 400 bp), although fragments outside of this size range may be used in certain embodiments. The fragments may be concatenated by ligation (e.g., by ligating the fragments directly to one another, or by ligating the fragments to one another via a junction adaptor, such as a double-stranded adaptor of 8-50 bp) or, alternatively, by overlap extension (e.g., by ligating the fragments an adaptor and concatenating the adapter-ligated fragments by overlap extension). As would be apparent, in some embodiments, the ends of the fragments may be blunted first if the fragments are going to be directly ligated to one another. In embodiments in which the fragments are ligated to one another via a junction adaptor, the fragments may be optionally A-tailed prior to ligation to an adaptor with single base 3' T overhangs. Alternatively, the fragments may be T-tailed and ligated to adaptors with A overhangs, C-tailed and ligated to adaptors with G overhangs, or G-tailed and ligated to adaptors with C overhangs, etc. Each of these combinations of overhangs is designed to ensure that adaptors can only ligate to fragments (and vice versa) and that adaptor-adaptor ligation and fragment-fragment ligation cannot occur. As a result, the concatemer formed will consist of repeated fragment-adaptor units, facilitating breakpoint recognition when analyzing the sequencing data. In certain embodiments, a first portion of a sample may be treated to add a single nucleotide overhang (e.g., an A), and a second portion of a sample may be treated to add a single nucleotide overhang that is complementary to the first portion of the sample (e.g., a T). After this treatment, the two portions of the sample can be combined and ligated to one another to produce a concatemer in which the fragments from the first portion (which may be tailed with an A, for example) alternate with the fragments from the second portion (which may be talked with a T, for example).

The concatenated DNA may comprise at least a thousand or at least ten thousand concatenated DNA molecules, and each molecule may contain at least 3, at least 5, at least 10, at least 50, at least 100, at least 500, or at least 1000 fragments that are joined one another in a random order and orientation.

Next, the method comprises sequencing fragments of the concatenated DNA, or amplification products thereof, to produce a plurality of sequence reads. In some embodiments, the concatenated DNA may be sequenced directly (i.e., without amplification). In these embodiments, the concatenated DNA may be fragmented to a desired length (e.g., a median length that is 50 nt to 1000 nt or 100 nt 500 nt longer than the length of the initial fragments), ligating the fragmentation products to adaptors (where these steps may be done separately or by tagmentation, see, e.g., Caruccio, Methods Mol. Biol. 2011; 733:241-55), and sequencing the ligation products directly. In other embodiments (and as shown in FIG. 1) the method may comprise amplifying the concatenated DNA between the concatenation and sequencing steps. In some embodiments, the amplification may be done by fragmenting the concatenated DNA to a desirable size (e.g., a median length that is 50-500 nt longer than the length of the initial fragments), adding an adaptor (e.g., an asymmetric adaptor) to the fragments, and amplifying the fragments by PCR using primers that hybridize to the adaptor sequences. As noted above, the fragmentation and adaptor ligation steps may be mediated by a transposase (see, e.g., Caruccio, Methods Mol. Biol. 2011; 733:241-55), in which case the steps may be done simultaneously, i.e., in the same reaction using a process that is often referred to as "tagmentation". In other embodiments, the fragmenting may be done mechanically (e.g., by sonication, nebulization, or shearing) or using a double stranded DNA "dsDNA" fragmentase enzyme (New England Biolabs, Ipswich MA). In some of these methods (e.g., the mechanical and fragmentase methods), after the DNA is fragmented, the ends are polished and A-tailed prior to ligation to the adaptor. Alternatively, the ends may be polished and ligated to adaptors in a blunt-end ligation reaction. In some embodiments, the concatenated DNA may be amplified using a whole genome amplification method (e.g., MDA, MALBAC or PicoPLEX), which methods can be tailored to produce "sequence ready" amplicons of a desired length (e.g., amplicons that have sequencing-compatible adaptor sequences at their ends). The sequenced fragments, or amplification products thereof, may have a median length in the range of 200 bp to 2 kb, or, a length that is below 1 kb such as in the range of 50 bp to 500 bp, or 80 bp to 400 bp, although fragments having a median size outside of this range may be used.

In some embodiments, fragments are attached to a generic asymmetric adaptor before amplification thereby allowing the identification of sequencing reads that derive from either the top or bottom strand of a double-stranded fragment. This approach can be used in error-correction based on the idea that for a true DNA mutation, complementary substitutions should be present on both strands and, as such, a mutation can only be called with confidence if it is present in sequences from both strands.

As would be apparent, the primers used for amplification may be compatible with use in any next generation sequencing platform in which primer extension is used, e.g., Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al. (Nature 2005 437: 376-80); Ronaghi et al. (Analytical Biochemistry 1996 242: 84-9); Shendure et al. (Science 2005 309: 1728); Imelfort et al. (Brief Bioinform. 2009 10:609-18); Fox et al. (Methods Mol Biol. 2009; 553:79-108); Appleby et al. (Methods Mol Biol. 2009; 513:19-39) English et al. (PLoS One. 2012 7: e47768) and Morozova and Marra (Genomics. 2008 92:255-64), which are incorporated by reference for the general descriptions of the methods and the particular steps of the methods, including all starting products, reagents, and final products for each of the steps.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads.

As shown in FIG. 1, at least some of the sequence reads comprise: (i) at least the sequence of the 3' and/or 5' ends of a fragment that corresponds to the locus of interest (which correspond to the fragment's breakpoints); and (ii) sequence of one or both of the fragments that flank that fragment in the concatenated DNA. Imagine two different molecules with the same (i) 5'/3' fragmentation breakpoints. The two molecules can be disambiguated if concatenated to one or more different (ii) flanking fragments. In some cases, the sequence corresponding to the fragment that flanks the fragment of the locus of interest may be the sequence of the end of the flanking fragment (i.e., adjacent to the breakpoint of the fragment) and, as such, the identity of the fragment that flanks the fragment of the locus of interest in the concatenated DNA may be determined using a sequence of at least 10, at least 20 or at least 30 nucleotides that is close to the breakpoint of that fragment. As noted above, in some cases, the initial DNA fragments may be concatenated to one another via a junction adaptor, in which the breakpoints of the fragments may be readily identified by identifying the junction adaptor sequence. In embodiments in which the initial DNA fragments are concatenated to one another directly, the breakpoints of the fragments may be identified by comparing the sequence reads to a reference genome and, if a first part of a sequence read maps to one location in the genome and a second part of the sequence (which is adjacent to the first part) read maps to another location in the genome, then the breakpoint is between the first and second parts.

Figure 2:
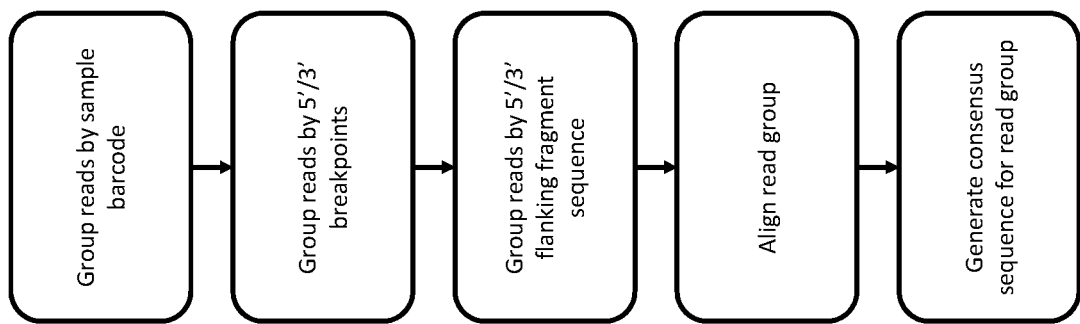
FIG. 2 shows a flow chart illustrating an exemplary bioinformatics workflow. The first three steps can in theory be performed in any order.

The sequence reads may be processed and grouped in any convenient way. In some implementations, initial processing of the sequence reads may include identification of molecular barcodes (including sample identifier sequences or sub-sample identifier sequences), and/or trimming reads to remove low quality or adaptor sequences. In addition, quality assessment metrics can be run to ensure that the dataset is of an acceptable quality. After initial processing and as shown in FIG. 2, the sequence reads may be grouped by grouping the sequence reads that corresponds to the locus of interest using, for each of the grouped sequence reads: (i) the 3' and/or 5' end sequences of a fragment corresponding to a locus of interest; and/or (ii) a sequence that flanks the sequences of a fragment corresponding to a locus of interest, i.e., the identity of the "flanking sequence". In other words, the sequence reads that correspond to a locus of interest may be grouped by a) one or both of the fragmentation breakpoints of the fragment corresponding to the locus of interest and/or b) the identity of one or more of the fragments that were joined to the fragment corresponding to locus of interest in the concatenation step.

Assuming that the initial fragments (i.e., the fragments that were concatenated) were made by fragmenting a more intact sample in a random or semi-random fashion, different fragments having the same sequence can be distinguished by their fragmentation breakpoint. As such, grouping the sequence reads by their fragmentation breakpoints provides a way to determine if a particular sequence (e.g., a sequence variant) is present in more than one starting molecule. For example, if two groups of sequence reads that have different fragmentation breakpoints contain a sequence variation, then one can be more confident that the sequence variation is genuine than if the sequence variation is only present in a single group. Further, because the concatenation process is random, different molecules that correspond to a locus of interest can be distinguished by the fragments that they are ligated to. For example if two fragments correspond to a locus of interest are otherwise identical in sequence and have identical fragmentation breakpoints but are flanked by different fragments, then those molecules can be distinguished in the sequence reads.

As such, the method may be used to determine whether a potential sequence variation is a genuine mutation or an artifact. This method may comprise, after grouping: determining which groups of sequence reads contain a potential sequence variation for the locus of interest; and calculating a probability that the potential sequence variation is a genuine mutation or an artifact using: (i) the number of reads in the group that contain the potential sequence variation, (ii) the number of groups that contain the potential sequence variation, and (iii) the total number of groups corresponding to the locus of interest. This calculating step may incorporate an error model that estimates the likelihood that a given sequencing and/or PCR error might occur. Several sources of information can be used in this assessment including (1) a base transition probability matrix (Statistical Methods in Bioinformatics: An Introduction by Warren J. Ewens, Gregory R. Gran). In one embodiment, the matrix can be estimated during consensus sequence derivation. For example, the number of reads at a given position in a read group that either agree or disagree with the most likely consensus base can be used to estimate transition probabilities. (2) The sequence context of a variant, e.g. whether the variant is adjacent to a homopolymer run; (3) known sequencer error modalities, such as sequencing cycle number; and (4) performance characteristics of sequencing positive and/or negative controls.

As noted above, the confidence that a potential sequence variation is a genuine sequence variation (rather than a PCR or sequencing error) increases if it is represented in more than one group, particularly groups that are defined by a larger number of sequence reads.

In some embodiments, the nucleic acids sequenced in the sequencing step may be enriched by target enrichment, many methods for which are known. In some embodiments, the enrichment may be done by hybridization to a probe, e.g., by SURESELECT™, which may involve hybridizing the amplification products to an oligonucleotide (e.g., RNA) probe that contains an affinity tag (e.g., biotin) to the amplification products. The resultant duplexes can be separated from other molecules' products by binding the oligonucleotide to a solid support and washing, and the target molecules can be released. Target enrichment can also be done using target-specific primers, by PCR amplification (see, e.g., US20130231253).

In some embodiments, the amplicons sequenced in the sequencing step may be selected by size (e.g., AMPure XP beads) so that shorter amplicons (of 200-300 bp) can be sequenced.

In some embodiments, sample identifiers (i.e., a sequence that identifies the sample to which the sequence is added, which can identify the patient, or a tissue, etc.) can be added to the polynucleotides prior to sequencing, so that multiple (e.g., at least 2, at least 4, at least 8, at least 16, at least 48, at least 96 or more) samples can be multiplexed. In these embodiments, the sample identifier can be present in an adaptor added after fragmentation of the concatenated DNA, for example. In some embodiments, the adaptor may comprise a sample identifier sequence that identifies the sample to which the adaptor is added.

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the fragments of DNA may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a DNA may be obtained from a subject, e.g., a human. In some embodiments, the sample analyzed may be a sample of cell-free "circulating" DNA (e.g., circulating tumor DNA) obtained from peripheral blood, e.g., from the blood of a patient or of a pregnant female. In some embodiments, the DNA comprises fragments of human genomic DNA. In some embodiments, the DNA may be obtained from a cancer patient. In some embodiments, the DNA may be made by extracting fragmented DNA from a patient sample, e.g., a formalin-fixed paraffin embedded tissue sample. In some embodiments, the patient sample may be cell-free DNA from a bodily fluid, e.g., peripheral blood. The DNA fragments used in the initial step of the method should be non-amplified DNA that has not been denatured beforehand.

The DNA in the initial sample may be made by extracting genomic DNA from a biological sample, and then fragmenting it. The fragments in the initial sample may have a median size that is below 1 kb (e.g., in the range of 50 bp to 500 bp, or 80 bp to 400 bp), although fragments having a median size outside of this range may be used. In other embodiments, the DNA in the initial sample may already be fragmented (e.g., as is the case for FPET samples and ctDNA).

In some embodiments, the amount of DNA in a sample may be limiting. For example, the initial sample of fragmented DNA may contain less than 200 ng of fragmented human DNA, e.g., 10 μg to 200 ng, 100 μg to 200 ng, 1 ng to 200 ng or 50 ng to 50 ng, or less than 10,000 (e.g., less than 5,000, less than 1,000, less than 500, less than 100 or less than 10) haploid genome equivalents, depending on the genome.

Bioinformatics Workflow

One implementation of an exemplary bioinformatics workflow is shown in FIG. 2.

The sequence reads may be analyzed by a computer and, as such, instructions for performing the steps set forth below may be set forth as programing that may be recorded in a suitable physical computer readable storage medium. The general principles of some of the analysis steps are described below.

The informatics steps of the above-described method can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of the computer is controlled primarily by an operating system, which is executed by the central processing unit. The operating system can be stored in a system memory. In some embodiments, the operating system includes a file system. In addition to an operating system, one possible implementation of the system memory includes a variety of programming files and data files for implementing the method described below. In certain cases, the programming can contain a program, where the program can be composed of various modules, and a user interface module that permits a user to manually select or change the inputs to or the parameters used by the program. The data files can include various inputs for the program.

In certain embodiments, instructions in accordance with the method described herein can be coded onto a computer-readable medium in the form of "programming," where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programs that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

In any embodiment, data can be forwarded to a "remote location," where "remote location," means a location other than the location at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

Some embodiments include implementation on a single computer, or across a network of computers, or across networks of networks of computers, for example, across a network cloud, across a local area network, on hand-held computer devices, etc. In certain embodiments, one or more of the steps described herein are implemented on a computer program(s). Such computer programs execute one or more of the steps described herein. In some embodiments, implementations of the subject method include various data structures, categories, and modifiers described herein, encoded on computer-readable medium(s) and transmissible over communications network(s).

Software, web, internet, cloud, or other storage and computer network implementations of the present invention could be accomplished with standard programming techniques to conduct the various assigning, calculating, identifying, scoring, accessing, generating or discarding steps.

The following patent publications are incorporated by reference for all purposes, particularly for methods by which nucleic acid molecules may be manipulated, reagents for doing the same, for sequencing library preparation workflow, sequencing methods, data processing methods, and for definitions of certain terms: U.S. Pat. No. 8,481,292, WO2013128281, and Casbon (Nuc. Acids Res. 2011, 22 e81), US20150044678, US20120122737, U.S. Pat. No. 8,476,018 and all references cited above and below.

Utility

As would be readily apparent, the method described above may be employed to analyze any type of sample, including, but not limited to samples that contain heritable mutations, samples that contain somatic mutations, samples from mosaic individuals, pregnant females (in which some of the sample contains DNA from a developing fetus), and samples that contain a mixture of DNA from different sources. In certain embodiments, the method may be used identify a minority variant that, in some cases, may be due to a somatic mutation in a person.

In some embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which may be associated with breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma (see, e.g., Chial 2008 Proto-oncogenes to oncogenes to cancer. Nature Education 1:1). Other oncogenic mutations (which may be somatic mutations) of interest include mutations in, e.g., APC, AXIN2, CDH1, GPC3, CYLD, EXT1, EXT2, PTCH, SUFU, FH, SDHB, SDHC, SDHD, VHL, TP53, WT1, STK11/LKB1, PTEN, TSC1, TSC2, CDKN2A, CDK4, RB1, NF1, BMPR1A, MEN1, SMAD4, BHD, HRPT2, NF2, MUTYH, ATM, BLM, BRCA1, BRCA2, FANCA, FANCC, FANCD2, FANCE, FANCF, FANCG, NBS1, RECQL4, WRN, MSH2, MLH1, MSH6, PMS2, XPA, XPC, ERCC2-5, DDB2 or MET, which may be associated with colon, thyroid, parathyroid, pituitary, islet cell, stomach, intestinal, embryonal, bone, renal, breast, brain, ovarian, pancreatic, uterine, eye, hair follicle, blood or uterus cancers, pilotrichomas, medulloblastomas, leiomyomas, paragangliomas, pheochromocytomas, hamartomas, gliomas, fibromas, neuromas, lymphomas or melanomas. In some embodiments, the method may be employed to detect a somatic mutation in genes that are implicated in cancer, e.g., CTNNB1, BCL2, TNFRSF6/FAS, BAX, FBXW7/CDCl$_4$, GLI, HPVE6, MDM2, NOTCH1, AKT2, FOXO1A, FOXO3A, CCND1, HPVE7, TAL1, TFE3, ABL1, ALK, EPHB2, FES, FGFR2, FLT3, FLT4, KRAS2, NTRK1, NTRK3, PDGFB, PDGFRB, EWSR1, RUNX1, SMAD2, TGFBR1, TGFBR2, BCL6, EVI1, HMGA2, HOXA9, HOXA11, HOXA13, HOXC13, HOXD11, HOXD13, HOX11, HOX11L2, MAP2K4, MLL, MYC, MYCN, MYCL1, PTNP1, PTNP11, RARA, SS18 (see, e.g., Vogelstein and Kinzler 2004 Cancer genes and the pathways they control. Nature Medicine 10:789-799). The method of embodiment may be employed to detect any somatic mutation that is implicated in cancer which is catalogued by COSMIC (Catalogue of Somatic Mutations in Cancer), data of which can be accessed on the internet.

Other mutations of interest include mutations in, e.g., ARID1A, ARID1B, SMARCA4, SMARCB1, SMARCE1, AKT1, ACTB/ACTG1, CHD7, ANKRD11, SETBP1, MLL2, ASXL1, which may be at least associated with rare syndromes such as Coffin-Siris syndrome, Proteus syndrome, Baraitser-Winter syndrome, CHARGE syndrome, KBG syndrome, Schinzel-Giedion syndrome, Kabuki syndrome or Bohring-Opitz syndrome (see, e.g., Veltman and Brunner 2012 De novo mutations in human genetic disease. Nature Reviews Genetics 13:565-575). Hence, the method may be employed to detect a mutation in those genes.

In other embodiments, the method may be employed to detect a mutation in genes that are implicated in a variety of neurodevelopmental disorders, e.g., KAT6B, THRA, EZH2, SRCAP, CSF1R, TRPV3, DNMT1, EFTUD2, SMAD4, LIST, DCX, which may be associated with Ohdo syndrome, hypothyroidism, Genitopatellar syndrome, Weaver syndrome, Floating-Harbor syndrome, hereditary diffuse leukoencephalopathy with spheroids, Olmsted syndrome, ADCA-DN (autosomal-dominant cerebellar ataxia, deafness and narcolepsy), mandibulofacial dysostosis with microcephaly or Myhre syndrome (see, e.g., Ku et al 2012 A new paradigm emerges from study of de novo mutations in the context of neurodevelopmental disease. Molecular Psychiatry 18:141-153). The method may also be employed to detect a somatic mutation in genes that are implicated in a variety of neurological and neurodegenerative disorders, e.g., SCN1A, MECP2, IKBKG/NEMO or PRNP (see, e.g., Poduri et al 2014 Somatic mutation, genetic variation, and neurological disease. Science 341(6141):1237758).

In some embodiments, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may indicate the presence and/or quantity of minority variant(s) in the sample. Once generated, the report may be forwarded to another location (which may be the same location as the first location), where it may be interpreted by a health professional (e.g., a clinician, a laboratory technician, or a physician such as an oncologist, surgeon, pathologist or virologist), as part of a clinical decision.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

Theoretical Background

Cell-free or circulating tumour DNA (ctDNA) is tumour DNA circulating freely in the blood of a cancer patient. Protocols to extract ctDNA generally aim to reduce contamination with normal DNA from leukocytes. This is achieved by rapid processing of whole blood by centrifugation to remove all cells, and analysis of the remaining plasma. ctDNA is highly fragmented, with a mean fragment size ~165 bp. Newman et al (Nat Med. 2014 20: 548-54) made libraries from 7-32 ng ctDNA isolated from 1-5 mL plasma. This is equivalent to 2,121-9,697 haploid genomes (assuming 3.3 µg per haploid genome). This range represents the maximum number of unique molecules that can be captured and sequenced. In practice the maximum number of molecules that can be captured is reduced by random fragmentation of regions covered by bait targets and inefficiencies during library preparation and target recovery.

Different library preparation methods and next generation sequencing (NGS) chemistries have their own systematic error profiles. It is possible to correct systematic errors, in part at least, that are correlated with known parameters including sequencing cycle-number, strand, sequence-context and base substitution probabilities (Meacham et al BMC Bioinformatics. 2011 12: 451). Random errors can be mitigated by replicate sequencing. However, neither method is sufficient if attempting to detect, with high specificity, a minority variant with frequency of $\leq$~3%. To improve error-detection and correction, several groups have used a repeat-code approach. The idea is to sequence copies of the same molecule. The copies are then aligned and a majority-vote used to generate a consensus sequence, which removes most of the errors. In addition, differences between each copy and the consensus sequences can be used to build up an error-model of a specific genomic region, which can then be applied to clean-up consensus sequences. For example, see Shugay et al. 2014 (Towards error-free profiling of immune repertoires. Nature Methods 11, 653-655 (2014)).

Four main methods can be applied to identify copies of the same molecule: (1) fragmentation breakpoints; (2) orientation of a DNA insert compared to surrounding adaptor sequences; (3) DNA barcodes and (4) physical separation.

If, by chance, two molecules have the same 5' and 3' breakpoints then one might incorrectly group reads and attempt to generate a consensus sequence. This could result in a false negative if a variant base was not called as part of the consensus sequence (e.g. if there were a greater number of, or higher quality, reads including a non-variant base). Additionally, an error model could be tricked into assuming that a variant base position was error-prone when in fact genuine calls are mixed from two, or more, different molecules. To mitigate this effect Newman et al. (2014) classified unique molecules as those with unique 5' and 3' breakpoints and 100% sequence identity, ignoring low quality base calls. This prevents false negative variants but is likely to increase false-positive calls owing to grouping of reads with errors. Newman et al. (2012) appear aware of this deficiency as they discuss implementing molecular tagging approaches to improve data quality.

To estimate the frequency of molecules with identical 5' and 3' breakpoints, one can make several simplifying assumptions: (1) breakpoints are randomly distributed; (2) to be captured a fragment must have 100% match to an RNA bait; and (3) that the library has a fixed sized range between 120-165 bp. For example, imagine a fragment where a 5' breakpoint maps 25 bp upstream of the RNA bait. To be within the fixed library size range the 5' breakpoint could be associated with any of 20 different 3' breakpoints. The same calculation can be performed for each of the possible 5' and 3' breakpoints that generate fragments within the size range. The total number of breakpoints can be calculated using: $\Sigma_{d=0}^{45} d+1$ where d is the difference in length between the maximum fragment length and the RNA bait length. In the above example, d=45 giving 1,081 breakpoints. Next, we can estimate the number of duplicate molecules using collision theory. The expected total number of times a selection will repeat a previous selection as x integers are chosen from a list of y integers (1, y) equals:

$$x - y + y\left(\frac{y-1}{y}\right)^x.$$

In our case, this can be paraphrased as the expected total number of times a captured molecule x will have the same two breakpoints as another captured molecule, where y is the number of molecules with different breakpoints in the library. For example, if x=1,000 and y=1,081 then 347 captured molecules are expected to have the same breakpoints as another captured molecule. In practice, the number of molecules that cannot be uniquely identified is likely higher than 347 because some of the 1,081 breakpoint combinations are likely to be observed more often than others, owing to the distribution of fragment sizes around a mean length and biases in fragmentation breakpoints. This suggests that one needs information in addition to the fragmentation breakpoints in order to uniquely identify molecules for error-correction.

DNA barcodes can be used on their own, or in addition with fragmentation breakpoints, to help identify duplicate molecules. There is an important distinction between methods where DNA barcodes are derived from adaptor sequences (made from oligonucleotides) and the case where DNA barcodes are derived from the random assortment and ligation of different genomic DNA sequences. If adaptor derived barcodes are attached en masse, they are added to template DNA before amplification and great care must be taken to ensure that residual adaptors are removed before amplification. These restrictions are not necessary if using the current approach, where barcodes derive from genomic DNA sequences. In addition, adaptor based tagging usually requires that the pool of barcode sequences are carefully synthesized and/or pooled before tagging. If barcodes are degenerate then there can be bias. If barcodes are pooled from individual synthesis reactions then care must be taken not to over- or under-represent individual barcode sequences. This restriction does not occur in the concatenation method where each fragment is randomly associated with two flanking fragments.

Physical separation methods include clonal amplification in a microdroplet or on a solid-surface (e.g. an Illumina flow-cell). Microdroplet methods generally rely on limiting dilution of template where each microdroplet contains only a fraction of the total genome (digital PCR, RainDance Technologies' Thunderstorm platform for target enrichment or 10× Genomics GemCode system). Current physical methods require complex microfluidics.

Example

The "Concatanation" Approach

Patient plasma DNA is end-repaired to yield blunt-end fragments with 5'-phosphates and 3'-hydroxyl termini Next, end-repaired fragments are ligated into concatemers by T4 DNA ligase. Concatemers are likely to be a mixture of linear and circular molecules. Linear molecules are favored in a small ligation volume (i.e. high DNA concentration). Ignoring the termini of linear concatemers, each concatenated fragment is juxtaposed between two fragments from different regions of the genome. Because of the huge diversity of potential fragments in the human genome the probability that two fragments have the same breakpoints and adjacent concatemer fragments is small.

Concatemers are amplified by devised WGA methods, e.g., MALBAC or PicoPLEX, which use semi-degenerate primers and multiple linear extensions followed by PCR. The WGA methods can also tag amplicons with Illumina NGS adaptor sequences. ctDNA fragments have a mean length of ~165 base-pairs. The size distribution of amplicons generated by PicoPLEX DNA-Seq is 200-9,000 bp versus 400-1,900 for MALBAC WGA (excluding adaptors), however these methods may be tailored to produce smaller amplicons, as desired. The ideal insert size for some implementations is ~200-250 bp because this is likely to include the ~165 bp fragment of interest and limited sequence from 5' and 3' adjacent fragments. Longer amplicons e.g. 1,000 bp are likely to include multiple concatemer fragments. Longer amplicons are deleterious during hybridization capture and NGS because: (1) they PCR with reduced efficiency; (2) a higher proportion of sequenced bases map off-target; and (3) a target positioned centrally in an amplicon might not be covered by paired-end reads. The simplest solution is to use a size selection (e.g. AMPure XP beads). Alternatively, PCR conditions could be optimized for shorter ~200-250 amplicons (e.g. by reducing the extension time during the thermocycling program).

In an alternative approach, the concatemers could be re-fragmented e.g. by sonication or transposon methods into shorter ~200-250 bp fragments before amplification by PCR. However, this approach would lose some of the advantages of the linear extension cycles used in the WGA methods.

Amplicons can be used as template in an Agilent SureSelect hybridisation capture. SureSelect RNA baits will capture both the ~165 bp target but also 35-85 bp from the two neighbouring fragments. After sequencing, custom scripts are used to identify: (1) on-target reads, (2) breakpoints between concatemers, and (3) adjacent concatemer sequences. Reads are then grouped using fragment 5' and 3' breakpoints in addition to the 5' and 3' sequences of adjacent fragments. Errors can be corrected using data from: (1) the estimated number of target molecules captured, (2) overlapping amplicons, (3) majority-vote consensus sequences, and (4) error models derived from majority-vote consensus sequences.

For ease of description, the method described in this section does not include adaptor ligation before concatenation. However, concatemer breakpoints may be difficult to identify with sufficient sensitivity or in a reasonable time, and fragments that contain genomic breakpoints might be difficult to identify unless multiple genomic fragments are captured and sequenced. To help identify these events, a constant region can be inserted between juxtaposed fragments in the concatemer. Junctions could be readily identified by, for example, using a sequence that does not naturally exist in the genome being sequenced.

That which is claimed is:

1. A method of sequencing, comprising:
   (a) concatenating a plurality of molecules of fragmented genomic DNA to each other to produce concatenated DNA that comprises multiple molecules of the DNA joined together, wherein:
      (i) the plurality of molecules are ligated to an adaptor and then concatenated by an overlap extension reaction that comprises overlapping the ligation products with one another, or
      (ii) the plurality of molecules are concatenated by ligation to one another via junction adaptors;
   (b) fragmenting the concatenated DNA to produce fragments of concatenated DNA; and
   (c) sequencing the fragments of concatenated DNA, or amplification products thereof, to produce a plurality of sequence reads; and
   (d) grouping the sequence reads that correspond to a locus of interest using:
      one or more end sequences of a fragment of the locus of interest; and/or
      the flanking sequences of the fragment of the locus of interest,
      wherein sequence reads that are grouped together have the same 3' end, the same 5' end and/or the same flanking sequences.

2. The method of claim 1, further comprising:
   (e) identifying a potential sequence variation in the locus of interest by analysis of a group of sequence reads.

3. The method of claim 1, wherein:
   step (d) further comprises grouping the sequence reads according to their orientation, wherein sequence reads that are derived from the top strand of a double-stranded molecule are grouped together and sequence reads that are derived from the bottom strand of the same double-stranded molecule are grouped together; and the method further comprises:
      identifying potential sequence variation in a group of sequence reads that correspond to the top strand of a molecule; and
      determining if the potential sequence variation is in any of the sequence reads that correspond to the bottom strand of the same molecule.

4. The method of claim 1, wherein in step (a) the plurality of molecules are ligated to an adaptor and then concatenated by an overlap extension reaction that comprises overlapping the ligation products with one another.

5. The method of claim 1, wherein in (a) the plurality of molecules are ligated to one another via junction adaptors.

6. The method of claim 5, wherein in (a) the plurality of molecules are A-tailed and the junction adaptors are T-tailed.

7. The method of claim 1, wherein the method comprises, between steps (a) and (b), amplifying the concatenated DNA.

8. The method of claim 7, wherein the amplifying is done by a whole genome amplification method.

9. The method of claim 1, wherein the amplifying is done by fragmenting the concatenated DNA, adding adaptors to the fragments of concatenated DNA, and then amplifying the fragments of concatenated DNA by PCR.

10. The method of claim 9, wherein the fragmenting and adding adaptors is done by a transposase.

11. The method of claim 1, wherein the DNA of (a) is obtained from a cancer patient.

12. The method of claim 1, wherein the fragmenting of (b) is done by sonication, nebulization, or shearing.

* * * * *